US006436906B1

(12) United States Patent
Or et al.

(10) Patent No.: US 6,436,906 B1
(45) Date of Patent: Aug. 20, 2002

(54) 9-AMINO-14-MEMBERED MACROLIDES DERIVED FROM LEUCOMYCINS

(75) Inventors: Yat Sun Or, Cambridge; Nha Vo, Malden, both of MA (US); Jianchao Wang, Castro Valley, CA (US); Ly Tam Phan, Malden, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 09/824,318

(22) Filed: Apr. 2, 2001

(51) Int. Cl.[7] ................ A61K 31/70; C07H 17/08
(52) U.S. Cl. ............... 514/29; 514/28; 536/7.1; 536/7.2; 536/7.4
(58) Field of Search .............. 514/28, 29; 536/7.1, 536/7.2, 7.9

(56) References Cited

U.S. PATENT DOCUMENTS

| | | | |
|---|---|---|---|
| 4,048,306 A | 9/1977 | Maier et al. ............. 424/180 |
| 5,075,289 A | 12/1991 | Pariza et al. ............. 514/29 |
| 5,110,800 A | 5/1992 | Bonjouklian et la. ....... 514/29 |
| 5,140,014 A | 8/1992 | Maring et al. ............ 514/30 |
| 5,760,011 A | 6/1998 | Jaynes et al. ............ 514/30 |
| 6,124,269 A | 9/2000 | Phan et al. .............. 514/29 |

FOREIGN PATENT DOCUMENTS

| | | | |
|---|---|---|---|
| EP | 89109890.7 | 12/1989 | ......... C07H/17/08 |
| EP | 93117427.0 | 5/1994 | ......... C07H/17/08 |
| WO | PCT/IB94/00199 | 1/1995 | ......... C07D/407/12 |

*Primary Examiner*—Elli Peselev
(74) *Attorney, Agent, or Firm*—Gaetano D. Maccarone, Esq.

(57) ABSTRACT

Novel 9-amino-14-membered macrolides and pharmaceutically-acceptable compositions comprising a therapeutically effective amount of a compound of the invention in combination with a pharmaceutically acceptable carrier, a method for treating bacterial infections by administering to a mammal a pharmaceutical composition containing a therapeutically-effective amount of a compound of the invention and processes for the preparation of such compounds.

14 Claims, No Drawings

9-AMINO-14-MEMBERED MACROLIDES DERIVED FROM LEUCOMYCINS

REFERENCE TO RELATED APPLICATION

Reference is made to prior copending, commonly assigned patent application Ser. No. 09/747,578, filed Dec. 22, 2000.

TECHNICAL FIELD

The present invention relates to novel macrolides having antibacterial activity and useful in the treatment and prevention of bacterial infections. More particularly, the invention relates to novel 9-amino-14-membered ring analogs, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Natural macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). The most commonly used macrolides are erythromycin and josamycin.

Erythromycins A, represented by Formula (Ia),

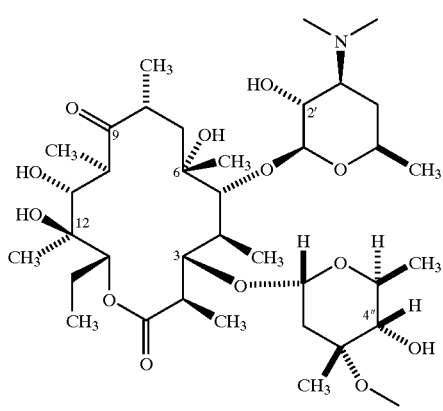

are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new macrolide compounds which possess one or more properties such as improved antibacterial activity, less potential for developing resistance, desired Gram-negative activity, and unexpected selectivity against target microorganisms. Consequently, numerous investigators have prepared chemical derivatives of erythromycin in an attempt to obtain analogs having modified or improved profiles of antibiotic activity.

Similarly, 16-membered ring macrolides like josamycin, kitasamycin, or tylosin have been extensively modified. Both josamycin and kitasamycin are members of the Leucomycin series. One group of the Leucomycin series is represented by Formula (Ib) and the various compounds are differentiated by the substituent at C-3 and C4".

(Ib)

| Leucomycin | R2 | R4 |
|---|---|---|
| A1 | H | C(O)CH2CHMe2 |
| (Kitasamycin) A5 | H | C(O)CH2CH2CH3 |
| A7 | H | C(O)CH2CH3 |
| A9 | H | C(O)CH3 |
| V(A11) | H | H |
| (Josamycin) A3 | C(O)CH3 | C(O)CH2CHMe2 |
| A4 | C(O)CH3 | C(O)CH2CH2CH3 |
| A6 | C(O)CH3 | C(O)CH2CH3 |
| A8 | C(O)CH3 | C(O)CH3 |
| U | C(O)CH3 | H |
| Miokamycin[1] | C(O)CH2CH3 | C(O)CH2CH2CH3 |
| Rokitamycin[2] | H | C(O)CH2CH2CH3 |

[1] 9-OAc; 3"-OAc
[2] 3"-OC(O)CH2CH3; 4"-OC(O)CH2CH2CH3

Typically, one drawback of 16-membered ring macrolides is their weaker antibacterial activity relative to the 14-membered ring macrolides. However, typically the 16-membered ring macrolides show some advantages over the 14-membered ring compounds derived from erythromycin with regard to gastrointestinal tolerance and activity against inducible resistant strain bacteria. Work in the macrolide field has focused primarily on structural modification of the 14-membered ring of erythromycin or the modification of the natural 16-membered ring macrolides.

For example, U.S. Pat. No. 4,048,306 discloses aldehyde-erythromycyclamine condensation products; U.S. Pat. No. 4,526,889 discloses an epimeric azahomoerythromycin A derivative; U.S. Pat. No. 5,075,289 discloses 9-R-azacyclic derivatives of erythromycin; U.S. Pat. No. 5,110,800 discloses 9-N-substituted derivatives of erythromycyclamine and U.S. Pat. No. 5,140,014 discloses certain 9-amino 16-membered tylonide derivatives.

There is a continuing need for novel 14-membered macrolide ring structures which overcome bacterial resistance.

SUMMARY OF THE INVENTION

The present invention provides a novel class of 9-amino-14-membered macrolide compounds possessing antibacterial activity toward Gram positive and Gram negative bacteria as well as macrolide resistant Gram positives.

In one embodiment, the present invention provides compounds represented by Formulas II or III, or a pharmaceutically acceptable salt, ester or prodrug thereof:

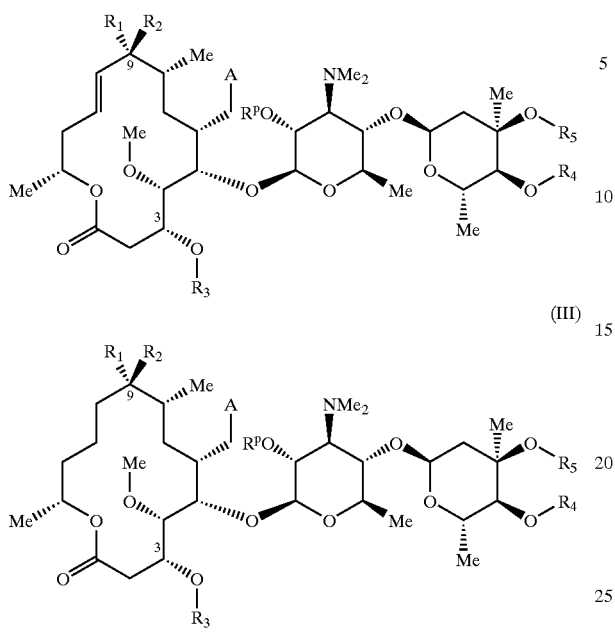

In Formulas II and III:

A is selected from the group consisting of;
(1) —CHO or a protected aldehyde
(2) —CH$_2$X, where X is selected from the group consisting of;
  a. hydroxy or protected hydroxy,
  b. halogen,
  c. —NR7R8, wherein R7 and R8 are each independently selected from hydrogen, aryl, substituted aryl, heterocyclic, substituted heterocyclic, C1–C6-alkyl, optionally substituted with aryl, substituted aryl, heterocyclic or substituted heterocyclic, C2–C6-alkenyl, optionally substituted with aryl, substituted aryl, heterocyclic or substituted heterocyclic and C2–C6-alkynyl, optionally substituted with aryl, substituted aryl, heterocyclic or substituted heterocyclic; or R7 and R8 taken together with the nitrogen atom to which they are connected form a 3- to 7-membered ring which, may optionally contain a hetero function selected from the group consisting of —O—, —NH—, —N(C1–C6-alkyl)—, —N(aryl)—, —N(heteroaryl)—, —S—, —S(O)— and —S(O)$_2$—,
  d. NR7C(O)—R9, where R7 is as previously defined and R9 is selected from the group consisting of,
    i. C1–C6-alkyl, optionally substituted with aryl, substituted aryl, heterocyclic or substituted heterocyclic,
    ii. aryl,
    iii. substituted aryl,
    iv. heterocyclic, and
    v. substituted heterocyclic
  e. —S(O)$_n$—(C1–C6-alkyl), optionally substituted with aryl substituted aryl, heterocyclic, or substituted heterocyclic, where n=0, 1 or 2,
  f. —S(O)$_n$—(C2–C6-alkenyl), optionally substituted with aryl, substituted aryl, heterocyclic or substituted heterocyclic, where n is as previously defined,
  g. —S(O)$_n$—(C2–C6-alkynyl), optionally substituted with aryl, substituted aryl, heterocyclic or substituted heterocyclic, where n is as previously defined,
  h. —S(O)$_n$—(aryl or heterocyclic), where n is as previously defined,
  i. —O—(aryl or heterocyclic),
(3) substituted or unsubstituted imidazole, arylimidazole or heteroarylimidazole,
(4) substituted or unsubstituted oxazole, aryloxazole or heteroaryloxazole,
(5) substituted or unsubstituted thioxazole, arylthioxazole or heteroarylthioxazole,
(6) substituted or unsubstituted imidazoline, arylimidazoline or heteroarylimidazoline,
(7) substituted or unsubstituted oxazoline, aryloxazoline or heteroaryloxazoline, and
(8) substituted or unsubstituted thioxazoline, arylthioxazoline or heteroarylthioxazoline, One of R1 and R2 is hydrogen and the other is —NR7R8 where R7 and R8 are as previously defined;

R3, R4 and R5 are each independently selected from the group consisting of,
(1) hydrogen,
(2) a hydroxy protecting group, and
(3) —C(O)—(C1–C12-alkyl), optionally substituted with aryl, substituted aryl, heterocyclic, substituted heterocyclic, —O—R7 or —NR7R8 where R7 and R8 are as previously defined; and $R^P$ is hydrogen or a hydroxy protecting group.

The compounds of the invention possess antibacterial activity toward Gram positive and Gram negative bacteria as well as macrolide resistant Gram positives.

DETAILED DESCRIPTION OF THE INVENTION

A first embodiment of the invention is a compound represented by Formula II as described above.

A second embodiment of the invention is a compound represented by Formula III as described above.

Representative compounds of the invention include, but are not limited to, those selected from the group consisting of:

Compound of Formula III: A=CHO, R1=NMe2, R2=H, R3=Ac, R4=C(O)CH2CHMe2, R5=H, $R^P$=H Compound of Formula III: A=CH(OMe)2, R1=NMe2, R2=H, R3=Ac, R4=C(O)CH2CHMe2, R5=H, $R^P$=H Compound of Formula II: A=CH(OMe)2, R1=NH2, R2=H, R3=Ac, R4=C(O)CH2CHMe2, R5=H, $R^P$=H.

Compound of Formula II: A=CH(OMe)2, R1=NMe2, R2=H, R3=Ac, R4=C(O)CH2CHMe2, R5=H, $R^P$=H Compound of Formula II: A=CHO, R1=NMe2, R2=H, R3=Ac, R4=C(O)CH2CHMe2, R5=H, $R^P$=H Compound of Formula II: A=CHO, R1=NHMe, R2=H, R3=Ac, R4=C(O)CH2CHMe2, R5=H, $R^P$=H Compound of Formula II: A=CHO, R1=NMeCH2C≡CH, R2=H, R3=Ac, R4=C(O)CH2CHMe2, R5=H, $R^P$=H Compound of Formula 11: A=CHO, R1=NMeCH2CH=CH2, R2=H, R3=Ac, R4=C(O)CH2CHMe2, R5=H, $R^P$=H Compound of Formula II: A=CHO, R1=NMeCH2(2-thienyl), R2=H, R3=Ac, R4=C(O)CH2CHMe2, R5=H, $R^P$=H Compound of Formula II: A=CHO, R1=NMeCH2(2-furanyl), R2=H, R3=Ac, R4=C(O)CH2CHMe2, R5=H, R$^P$=H Compound of Formula II: A=CHO, R1=NMeCH2(4-chlorophenyl), R2=H, R3=Ac, R4=C(O)CH2CHMe2, R5=H, R$^P$=H Compound of Formula II: A=CHO, R1=NMeCH2(2-pyridyl), R2=H, R3=Ac, R4=C(O)CH2CHMe2, R5=H, R$^P$=H Compound of Formula II: A=CHO, R1=NMeCH2(3-quinolyl), R2=H, R3=Ac, R4=C(O)CH2CHMe2, R5=H, R$^P$=H Compound of Formula II: A=CHO, R1=NMeCH2CH=CH(phenyl), R2=H, R3=Ac, R4=C(O)CH2CHMe2, R5=H, R$^P$=H Compound of Formula II: A=CHO, R1=NMeCH2CH=CH(2-pyridyl), R2=H, R3=Ac, R4=C(O)CH2CHMe2, R5=H, R$^P$=H Compound of Formula II: A=CHO, R1=NMeCH2C≡C(3-quinolyl), R2=H, R3=Ac, R4=C(O)CH2CHMe2, R5=H, R$^P$=H Compound of Formula II: A=CH2OH, R1=NMe2, R2=H, R3=Ac, R4=C(O)CH2CHMe2, R5=H, R$^P$=H Compound of Formula II: A=CH2N(CH3)CH2Ph, R1=NMe2, R2=H, R3=Ac, R4=C(O)CH2CHMe2, R5=H, R$^P$=H Compound of Formula II: A=CH2N(CH3)CH2CH2Ph, R1=NMe2, R2=H, R3=Ac, R4=C(O)CH2CHMe2, R5=H, R$^P$=H Compound of Formula II: A=CH2N(CH3)CH2CH2CH2Ph, R1=NMe2, R2=H, R3=Ac, R4=C(O)CH2CHMe2, R5=H, R$^P$=H Compound of Formula II: A=CH2N(CH3)CH2CH=CH2, R1=NMe2, R2=H, R3=Ac, R4=C(O)CH2CHMe2, R5=H, R$^P$=H Compound of Formula II: A=CH2N(CH3)CH2C≡CH, R1=NMe2, R2=H, R3=Ac, R4=C(O)CH2CHMe2, R5=H, R$^P$=H Compound of Formula II: A=CH2N(CH3)CH2CH=CH(3-quinolyl), R1=NMe2, R2=H, R3=Ac, R4=C(O)CH2CHMe2, R5=H, R$^P$=H Compound of Formula II: A=CH2N(CH3)CH2C≡C(5-pyrimidine), R1=NMe2, R2=H, R3=Ac, R4=C(O)CH2CHMe2, R5=H, R$^P$=H Compound of Formula II: A=CH2N(CH3)CH2C≡C(2-thienyl-(2-pyridyl)), R1=NMe2, R2=H, R3=Ac, R4=C(O)CH2CHMe2, R5=H, R$^P$=H Compound of Formula II: A=CH2N(CH3)CH2C≡C(3,5-dichlorophenyl), R1=NMe2, R2=H, R3=Ac, R4=C(O)CH2CHMe2, R5=H, R$^P$=H Compound of Formula II: A=CH2N(CH3)CH2C≡C(4-fluorophenyl), R1=NMe2, R2=H, R3=Ac, R4=C(O)CH2CHMe2, R5=H, R$^P$=H Definitions The terms "$C_1$–$C_3$-alkyl" or "$C_1$–$C_6$-alkyl" as used herein refer to saturated, straight-or branched-chain hydrocarbon radicals containing between one and three or one and six carbon atoms, respectively. Examples of $C_1$–$C_3$ alkyl radicals include methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl.

The term "$C_1$–$C_6$-alkoxy" as used herein refers to a $C_1$–$C_6$-alkyl group, as previously defined, attached to the parent molecular moiety through an oxygen atom. Examples of $C_1$–$C_6$-alkoxy, but are not limited to, methoxy, ethoxy, propoxy, isopropoxy, n-butoxy, tert-butoxy, neopentoxy and n-hexoxy.

The term "$C_1$–$C_3$-alkyl-amino" as used herein refers to one or two $C_1$–$C_3$-alkyl groups, as previously defined, attached to the parent molecular moiety through a nitrogen atom. Examples of $C_1$–$C_3$-alkyl-amino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as for example, hexane and toluene, and the like, halogenated hydrocarbons, such as, for example, methylene chloride, ethylene chloride, chloroform, and the like, heterocyclic compounds, such as, for example, tetrahydrofuran, N-methylpyrrolidinone, and the like and ethers such as for example, diethyl ether, bis-methoxymethyl ether and the like. Such compounds are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "aryl" as used herein refers to unsubstituted carbocyclic aromatic groups including, but not limited to, phenyl, 1- or 2-naphthyl and the like.

The term "$C_3$–$C_5$-cycloalkyl- and $C_3$–$C_7$-cycloalkyl" as used herein refers to carbocyclic groups of 3 to 5 or 3 to 7 carbon atoms, respectively, such as for example, cyclopropyl, cyclobutyl, cyclopentyl, cyclohexyl, and cycloheptyl.

The term "$C_1$–$C_3$-alkyl-$C_3$–$C_5$-cycloalkyl", as used herein refers to a $C_3$–$C_5$-cycloalkyl radical, as defined above, attached to a $C_1$–$C_3$-alkyl radical by replacement of a hydrogen atom on the latter.

The terms "halo" and "halogen" as used herein refer to an atom selected from fluorine, chlorine, bromine and iodine.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl" as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic" as used herein, refers to heterocycloalkyl and heteroaryl. The term "substituted heterocyclic", as used herein, refers to substituted heterocycloalkyl and substituted heteroaryl.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, f, for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "substituted aryl" as used herein refers to an aryl group as defined herein substituted by independent replacement of one, two or three of the hydrogen atoms thereon with F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-hetcroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$-$C_6$-alkyl, $SO_2$-aryl, $SO_2$-heteroaryl, $SO_2NH_2$, $SO_2NH$—$C_1$-$C_6$-alkyl, $SO_2NH$-aryl $SO_2NH$-heteroaryl, $C_1$-$C_6$-alkyl, $C_3$-$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl.

The term "substituted heteroaryl" as used herein refers to a heteroaryl group as defined herein substituted by independent replacement of one, two or three of the hydrogen atoms thereon with F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$-$C_6$-alkyl, $SO_2$-aryl, $SO_2$-heteroaryl, $SO_2NH_2$, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl.

The term "substituted heterocycloalkyl" as used herein, refers to a heterocycloalkyl group, as defined above, substituted by independent replacement of one, two or three of the hydrogen atoms thereon with F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$ -$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$-$C_6$-alkyl, $SO_2$-aryl, $SO_2$-heteroaryl, $SO_2NH_2$, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug Design*, American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a microdilution method. Minimal Inhibitory Concentration (MIC) was determined in 96 well microtiter plates utilizing the appropriate Mueller Hinton Broth medium (CAMHB) for the observed bacterial isolate. Antimicrobial agents were serially diluted (2-fold) in DMSO to produce a concentration range of 32 µg/ml to 0.0625 µg/ml.

The diluted compounds (2 µl/well) were then transferred into sterile, uninoculated CAMHB 0.2 mL) by use of a 96 fixed tip-pipetting station. The inoculum for each bacterial strain was standardized to $5\times10^5$ CFU/mL by optical comparison to a 0.5 McFarland turbidity standard. The plates were inoculated with 10 µl/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC.

Antibiotic control standards were included in alternate wells of the same 96 well plate as the antimicrobial agent of interest for testing. The selected control agent was chosen as a compound belonging to the same antibiotic class as the test compound and having known susceptibility patterns for the bacterial organism being tested.

All in vitro testing followed the guidelines described in the Approved Standards M7-A4 protocol published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulate matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the scheme and the examples that follow are: AIBN for azobisisobutyronitrile; Bu$_3$SnH for tributyltin hydride; CDI for carbonyldiimidazole; DBU for 1,8-diazabicyclo[5.4.0]undec-7-ene; DEAD for diethylazodicarboxylate; DMF for dimethyl formamide; DPPA for diphenylphosphoryl azide; EtOAc for ethyl acetate; MeOH for methanol; NaN(TMS)$_2$ for sodium bis(trimethylsilyl)amide; NMO for N-methylmorpholine N-oxide; TEA for triethylamine; THF for tetrahydrofuran; TPP for triphenylphosphine; DMAP for 4-N,N-dimethylamino pyridine; and TFA for trifluoroacetic acid.

Synthetic Methods

The compounds and processes of the present invention will be better understood in connection with the following synthetic schemes which illustrate the methods by which the compounds of the invention may be prepared. The groups A, R1, R2, R3, R4, and R$^p$ are as defined above unless otherwise noted below.

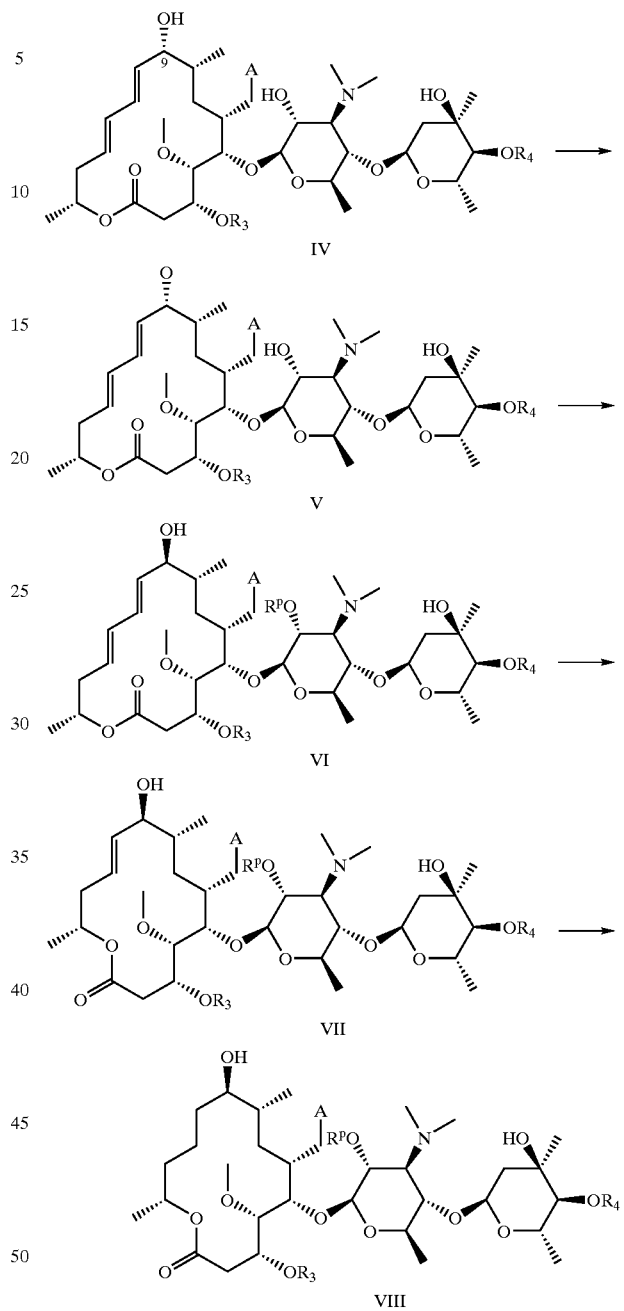

Scheme 1

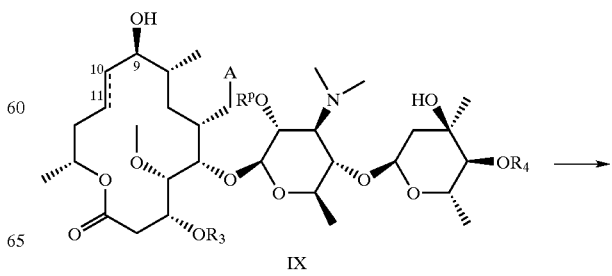

Scheme 2

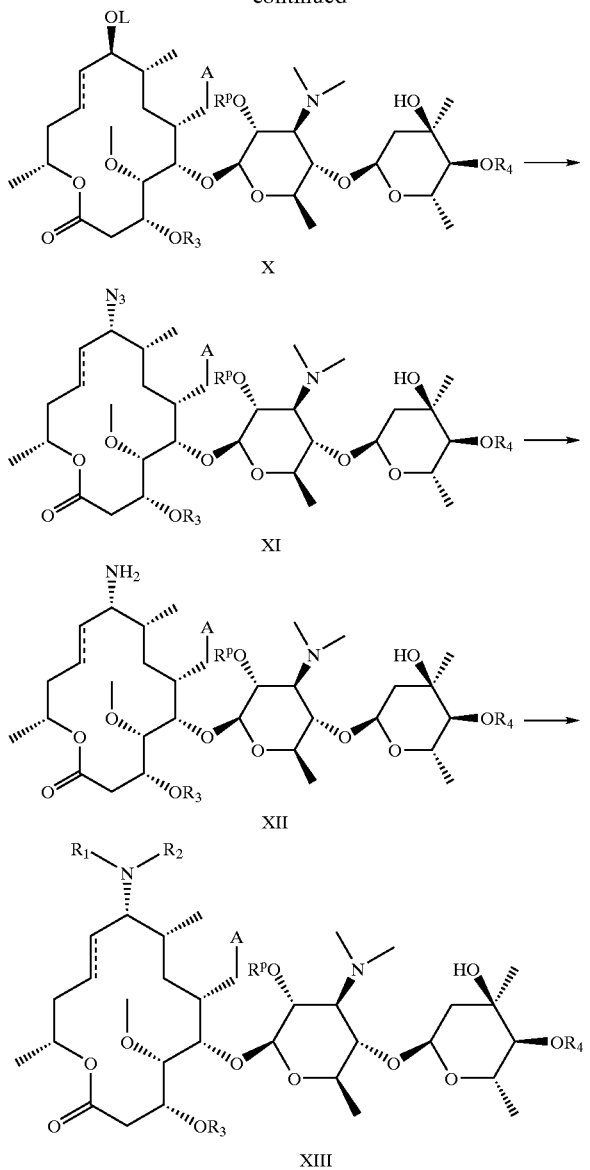

Process I.

The process of the invention for the preparation of the compounds of Formula II or III comprises reacting a compound of Formula IV (Scheme 1) where A, R3 and R4 are as previously defined with an oxidizing agent such as $MnO_2$, DDQ, $CrO_3$/pyridine, PCC, DCC, TPAP, and the like in an organic solvent such as methylene chloride, chloroform, benzene, toluene, DMF and the like at from room temperature to about 60° C. to provide the corresponding 9-ketone (Formula V). The preferred reaction condition employs $CrO_3$/pyridine as the oxidizing agent and methylene chloride as the solvent. Reduction of the dienone 2 with a hydride reducing agent such as NaBH4, LiBH4, or the like, optionally in the presence of an additive such as $CeCl_3$ to provide the 9-β-alcohol (Formula VI). Compounds of Formula VI undergo a ring contraction process which comprises reacting the compound with Grubbs' ruthenium alkylidene or benzylidene catalysts (see (a) U.S. Pat. No. 6,111,121. (b) Reviews: *Synlett*. 1999, 2, 267. (c) Reviews: Ivin, K. J.; Mol. J. C. *Olefin Metathesis and Metathesis Polymerization*, $2^{nd}$ ed.; Academic Press: New York, 1997. (d) *J. Org. Chem.* 1999, 64, 4798–4816. (e) *Angew. Chem., Int. Ed. Engl.* 1997, 36, 2036–2056. (f) *Tetrahedron* 1998, 54, 4413–4450) or Nolan's ruthenium catalyst (see (a) International Patent Application No. PCT/US99/20629; International Publication No. WO 00/15339. (b) *Org. Lett.* 2000, 2, 1517–1519. (c) *J. Org. Chem.* 2000, 65, 2204–2207.) or molybdenum catalysts (see (a) *J. Am. Chem. Soc.* 1990, 112, 3875. (b) *J. Am. Chem. Soc.* 1996, 118, 10926–10927.) optionally in the presence of additives such as ethylene, 1-hexene, isobutylene, titanium (IV) isopropoxide or aluminum (III) isopropoxide in an organic solvent such as dichlomethane, chloroform, toluene, benzene, THF, DMF and the like at from room temperature to about 100° C. for 1–7 days to provide a 14-membered ring contracted product, a compound of Formula VII. The preferred ruthenium catalysts are Nolan's catalyst (tricyclohexylphosphine[1,3-bis(2,4,6-trimethylphenyl)-imidazol-2-ylidene]benzylidene Ruthenium(IV)dichloride) or tricyclohexylphosphine[1,3-bis(2,4,6-trimethylphenyl)-4,5-dihydroimidazol-2-ylidene] benzylidene ruthenium(IV)dichloride and the preferred solvent is dichlomethane or toluene.

Compounds of Formula VII can be reduced to a saturated product where C10–C11 is a dihydro (Formula VIII) via hydrogenolysis methods by treating with palladium catalysts (palladium black, palladium on carbon), $RhCl(PPh_3)_3$ and the like in the presence of 1–4 atmospheres of hydrogen gas in an organic solvent such as methanol, ethanol, isopropanol, ethylacetate, DMF, and the like at from room temperature to about 60° C. for 1 hour to 2 days. Both compounds of Formula VII and VIII, represented by Formula IX, can be converted to 9-amino derivatives by reacting a compound of Formula IX with mesyl chloride or tosyl chloride in organic solvent such as methylene chloride, THF and the like at from about −78° C. to room temperature to provide a compound of Formula X, wherein L is a mesyl or tosyl, followed by treating the corresponding mesylate or tosylate with an azide nucleophile such as sodium azide, tetrabutyl ammonium azide, lithium azide, and the like in an organic solvent such as those described above to provide a compound of Formula XI. A compound of Formula XI can be reduced to an amino compound by reaction with triphenyl phosphine in an organic solvent such as THF, DMF and the like or water, or a combination thereof at from room temperature to about 100° C. to provide a compound of Formula XII. Alternatively, a compound of Formula XII could be obtained from a compound of Formula XI via hydrogenolysis methods as described earlier or via alkylation methods by treating a compound of Formula XII with an alkyl halide in an organic solvent such as those described above at from room temperature to about 100° C.

Process II.

Compounds of Formula II or III where A is CHO can be further derivatized to amino derivatives via reductive amination methods by treating with an amine compound in the presence of sodium borohydride or sodium cyanoborohydide and the like in an alcoholic solvent such as methanol, ethanol, or isopropanol at a pH of 2–6. Compounds of Formula II or III (such as compounds of Formula XIII of Scheme 2) where A is CHO can be further reduced to a corresponding alcohol where A is —$CH_2OH$ with various hydride reducing agents such as sodium borohydrides, lithium borohydrides, and the like.

EXAMPLES

The procedures described above for preparing the compounds of the present invention will be better understood in connection with the following examples, which are intended to be illustrative only and not limiting of the scope of the invention. Various changes and modifications to the disclosed embodiments will be apparent to those skilled in the art. Such changes and modifications, including without limitation, those relating to the chemical structures, substituents, derivatives, intermediates, syntheses, formulations and/or methods of the invention may be made without departing from the spirit of the invention and the scope of the appended claims.

Example 1

Compound of Formula III: A=CHO, R1=NMe2, R2=H, R3=Ac, R4=C(O)CH2CHMe2, R5=H, $R^P$=H Step 1a. Compound of Formula V: A=CHO, R3=Ac, R4=C(O)CH2CHMe2.

A solution of $CrO_3$ (7.0 g, 70 mmol) in water (7 mL) was added dropwise over 10 minutes to pyridine (30 mL) at 0° C. To the $CrO_3$ mixture, a solution of josamycin (6.6 g, 7.98 mmol) in pyridine (15 mL) was added, and stirred for 2 hours at room temperature. The mixture was diluted with water and extracted with dichloromethane. The organic solution was dried over anhydrous sodium sulfate, and concentrated under vacuum. The residue was purified by chromatography on silica gel (eluting with hexanes:ethyl acetate/1:5) to give the desired compound (2.87 g, 44%) as a white solid.

MS (ESI) m/z 826 (M+H)$^+$. $^{13}$C-NMR (100 MHz, CDCl$_3$): δ 203.0,201.0, 149.7, 144.4, 140.6, 136.3, 132.7, 129.1, 128.3, 125.4, 124.0, 122.4, 103.7, 97.1, 84.9, 77.8, 77.6, 77.1, 76.0, 73.0, 71.7, 69.5, 69.2, 68.8, 68.6, 63.6, 62.6, 44.3, 43.4, 43.0, 42.0, 41.8, 40.8, 36.8, 32.3, 30.9, 25.6, 25.5, 22.6, 22.5, 21.3, 20.6, 18.9, 18.0, 17.6.

Step 1b. Compound of Formula V: A=CH(OMe)2, R3=Ac, R4=C(O)CH2CHMe2, $R^P$=Bz

A solution of the compound from step 1a (1.37 g, 1.66 mmol) and Bz$_2$O (1.0 g, 4.42 mmol) in pyridine (20 mL) was stirred overnight at room temperature. The solution was concentrated under vacuum, diluted with dichloromethane (80 mL), washed with aqueous sodium bicarbonate solution, and dried over anhydrous sodium sulfate. The solvent was evaporated, and the residue was dissolved in methanol (60 mL). The pH of the methanol solution was adjusted to 3 by adding acetic chloride at 0° C. The solution was stirred overnight, neutralized with sodium bicarbonate, and concentrated. Purification on silica gel chromatography (eluting with toluene:acetone/5:1) gave the title compound (1.52 g, 94%) as a light yellow solid.

MS (ESI) m/z 976 (M+H)$^+$. $^{13}$C-NMR (100 MHz, CDCl$_3$): δ 203.9, 173.0, 170.1, 169.9, 164.4, 143.6, 139.6, 133.4, 133.0, 130.2, 129.8, 129.2, 128.8, 128.4, 125.4, 122.8, 100.6, 100.6, 97.2, 85.6, 77.5, 77.2, 75.8, 75.2, 72.9, 71.6, 69.6, 69.4, 69.0, 68.1, 63.6, 62.2, 54.2, 47.1, 44.3, 43.4, 41.9,41.8, 20 40.4, 36.8, 33.1, 32.1, 29.7, 25.7, 25.5, 22.66, 22.5, 21.2, 20.6, 19.0, 18.1, 17.9.

Step 1c. Compound of Formula VI: A=CH(OMe)2, R3=Ac, R4=C(O)CH2CHMe2, $R^P$=Bz

To a mixture of the compound from step 1b (1.39 g, 1.43 mmol) and CeCl$_3$.7H$_2$O (531 mg, 1.43 mmol) in methanol (4 mL) was added NaBH$_4$ (107.8 mg, 2.85 mmol) at −60° C. The mixture was stirred for 5 minutes, quenched with aqueous ammonium chloride solution, and extracted with dichloromethane. The organic solution was washed with aqueous sodium bicarbonate solution, dried over anhydrous sodium sulfate, and concentrated under vacuum. Purification with silica gel chromatography (eluting with toluene:acetone/5: 1) gave the desired compound (1.13 g, 82%) as a white solid.

MS (ESI) m/z 978 (M+H)$^+$. $^{13}$C-NMR (100 MHz, CDCl$_3$): δ 173.0, 170.2, 170.1, 164.4, 133.3, 132.9, 131.4, 130.3, 130.0, 129.8, 129.4, 129.2, 128.7, 128.4, 125.4, 102.3, 100.5, 97.1, 85.5, 77.6, 77.1, 76.4, sodium bicarbonate solution, dried over anhydrous sodium sulfate, and concentrated under vacuum. Purification with silica gel chromatography (eluting with toluene:acetone/5:1) gave the desired compound (1.13 g, 82%) as a white solid.

MS (ESI) m/z 978 (M+H)$^+$. $^{13}$C-NMR (100 MHz, CDCl$_3$): δ 173.0, 170.2, 170.1, 164.4, 133.3, 132.9, 131.4, 130.3, 130.0, 129.8, 129.4, 129.2, 128.7, 128.4, 125.4, 102.3, 100.5, 97.1, 85.5, 77.6, 77.1, 76.4, 75.9, 75.2, 73.0, 71.6, 69.6, 69.5, 69.2, 68.1, 63.6, 62.0, 52.6, 51.4, 43.4, 42.0, 41.8, 40.7, 36.8, 35.7, 32.4, 30.9, 30.2, 25.6, 25.4, 22.6, 22.5, 21.6, 21.3, 20.9, 20.4, 19.1, 18.1.

Step 1d. Compound of Formula VII: A=CH(OMe)2, R3=Ac, R4=C(O)CH2CHMe2, $R^P$=Bz

To a solution of the compound from step 1c (1.0 g, 1.02 mmol) in dichloromethane (50 mL) there was added Ti(OiPr)$_4$ (0.120 mL, 0.40 mmol) and refluxed for 20 minutes. The solution was cooled down to room temperature, degassed with nitrogen, and then Nolan catalyst (86 mg, 0.10 mmol) was added. The solution was stirred for 3 days at 50° C. under nitrogen, and concentrated under vacuum. Purification with silica gel chromatography (eluting with ethyl acetate) gave the desired compound (0.90 g, 92%) as a white solid.

MS (ESI) m/z 952 (M+H)$^+$. $^{13}$C-NMR (100 MHz, CDCl$_3$): δ 173.0, 170.5, 168.9, 164.4, 135.6, 133.3, 130.3, 129.7, 129.2, 128.7, 128.4, 127.3, 125.4, 101.5, 100.7, 97.1, 78.4, 77.6, 77.1, 75.9, 72.9, 71.5, 70.2, 69.6, 68.1, 63.6, 61.8, 53.8, 43.4, 42.0, 41.8, 38.1, 37.7, 36.8, 35.3, 31.4, 25.6, 25.4, 22.6, 22.5, 21.1, 19.1, 18.4, 18.1.

Step 1e. Compound of Formula VIII: A=CH(OMe)2, R3=Ac, R4=C(O)CH2CHMe2, $R^P$=Bz

A mixture of the compound from step 1d (0.54g, 0.568 mmol) and Pd(OH)$_2$/C (50 mg) in methanol (30 mL) was stirred under H$_2$ (attached with a balloon) overnight. The catalyst was filtered off. The solvent was evaporated to give the desired compound (0.53g, 98%) as white solid.

MS (ESI) m/z 954 (M+H)$^+$. $^{13}$C-NMR (100.5 MHz, CDCl$_3$): δ 173.1, 170.5, 169.0, 164.5, 133.4, 130.3, 129.9, 128.8, 101.5, 100.7, 97.2, 77.4, 75.9, 75.4, 73.6, 73.0, 71.7, 70.0, 69.6, 68.0, 63.6, 61.9, 54.1, 48.8, 43.4, 42.0, 41.8, 37.0, 34.3, 34.1, 33.6, 32.9, 32.7, 25.7, 25.5, 22.6, 22.6, 21.1, 21.0, 20.0, 19.1, 18.1, 15.8.

Step 1f. Compound of Formula X: A=CH(OMe)2, R3=Ac, R4=C(O)CH2CHMe2, C10C11-dihydro, $R^P$=Bz To a solution of the compound from step 1e (0.41 g, 0.43 mmol) in dichloromethane (30 mL) containing triethylamine (0.24 mL, 1.72 mmol) there was added MsCl (0.050 mL, 0.65 mmol) at 0° C. The solution was stirred overnight, washed with aqueous sodium bicarbonate, and dried over anhydrous sodium sulfate. The solvent was evaporated to give the desired compound (0.44 g, 100%).

MS (ESI) m/z 1032 (M+H)$^+$.

Step 1g. Compound of Formula XI: A=CH(OMe)2, R3=Ac, R4=C(O)CH2CHMe2, C10C11-dihydro, $R^P$=Bz To a solution of the compound from step 1f (0.44 g, 0.43 mmol) in DMF (15 mL) were added NaN$_3$ (1.0 g, 15.4 mmol) and NH$_4$Cl (0.5 g, 9.35 mmol). The mixture was stirred at 100° C. for 3 hours, diluted with water, and extracted with dichloromethane. Purification with silica gel chromatography (eluting with ethyl acetate) gave the desired compound (0.24 g, 50%) as a white solid.

MS (ESI) m/z 979 (M+H)$^+$. $^{13}$C-NMR (100 MHz, CDCl$_3$): δ 173.0, 170.5, 170.1, 164.4, 133.4, 130.1, 129.8, 128.7, 101.7, 100.8, 97.1, 87.2, 77.5, 77.1, 76.7, 75.8, 75.1, 72.9, 71.4, 70.5, 69.5, 68.2, 65.0, 63.6, 62.0, 53.7, 49.5, 43.4, 41.9, 41.8, 39.4, 34.4, 33.5, 31.4, 31.0, 30.8, 29.8, 29.6, 25.6, 25.4, 23.2, 22.5, 22.5, 20.8, 20.7, 19.0, 18.1, 16.1.

Step 1h. Compound of Formula XI: A=CH(OMe)2, R3=Ac, R4=C(O)CH2CHMe2, C10C11-dihydro, $R^P$=H A solution of the compound from step 1g (0.31 g, 0.32 mmol) in methanol (30 mL) was refluxed for 3 days. The solvent was evaporated under vacuum to give the crude desired product.

MS (ESI) m/z 875 (M+H)$^+$.

Step 1i. Compound of Formula XI: A=CHO, R3=Ac, R4=C(O)CH2CHMe2, $R^P$=H

To a solution of the crude compound from step 1h in acetonitrile (3 mL) were added water (15 mL) and TFA (0.073 mL, 0.95 mmol). The mixture was stirred overnight at room temperature, diluted with aqueous sodium bicarbonate and extracted with dichloromethane. The organic solution was dried over anhydrous sodium sulfate and concentrated under vacuum. Purification with silica gel chromatography (eluting with ethyl acetate) gave the desired compound (0.128 g, 51% yield).

MS (ESI) m/z 829 (M+H)$^+$. $^{13}$C-NMR (100 MHz, CDCl$_3$): δ 201.0, 173.1, 171.2, 170.2, 103.6, 97.2, 86.3, 78.3, 77.5, 77.1, 76.1, 75.2, 73.1, 71.6, 70.1, 69.5, 68.8, 64.6, 63.7, 62.4, 43.6, 43.4, 42.1, 41.8, 39.7, 34.7, 33.7, 30.3, 29.8, 25.7, 25.5, 23.1, 22.6, 22.6, 21.1, 20.9, 18.9, 18.0, 16.3.

Step 1j. Compound of Formula III: A=CHO, R1=H, R2=N(Me)2, R3=Ac, R4=C(O)CH2CHMe2, R5=H, $R^P$=H A mixture of the compound from step 1i (100 mg, 0.12 mmol), formaldehyde (2 mL, 37% aqueous solution) and Pd(OH)$_2$/C (20 mg) in methanol (20 mL) was stirred overnight under hydrogen (attached with a balloon). The catalyst was filtered off and the solvent was evaporated under vacuum. Purification with silica gel chromatography (eluting with ethyl acetate:triethylamine/5:1) gave the title compound (72.2 mg, 74%) as a light yellow solid.

MS (ESI) m/z 931 (M+H)$^+$. $^{13}$C-NMR (100 MHz, CDCl$_3$): δ 201.4, 173.1, 170.7, 170.1, 104.0, 97.2, 85.3, 78.7, 77.4, 77.2, 76.0, 74.3, 73.1, 71.7, 70.3, 69.5, 68.9, 64.2, 63.7, 62.3, 43.5, 42.3, 42.1, 41.8, 39.3, 35.3, 30.3, 29.8, 25.7, 25.5, 22.6, 22.6, 21.0, 20.8, 19.0, 18.1, 18.0.

Example 2

Compound of Formula III: A=CH(OMe)2, R1=NMe2, R2=H, R3=Ac R4=C(O)CH2CHMe2, R5=H, $R^P$=H Step 2a: Compound of Formula III: A=CH(OMe)2, R1=NMe2, R2=H, R3=Ac, R4=C(O)CH2CHMe2, R4=H, R5=Bz.

A mixture of the compound from step 1g of Example 1 (300 mg, 0.307 mmol), formaldehyde (2 mL, 37% aqueous solution) and Pd(OH)$_2$/C (30 mg) in methanol (30 mL) was stirred overnight under hydrogen (attached with a balloon). The catalyst was filtered off and the solvent was evaporated under vacuum. Purification with silica gel chromatography (eluting with 5:1 ethyl acetate:triethylamine) gave the desired compound (97 mg, 33%) as a light yellow solid.

MS (ESI) m/z 981 (M+H)$^+$. $^{13}$C-NMR (100 MHz, CDCl$_3$): δ 173.0, 170.0, 169.7, 164.5, 133.3, 130.3, 129.9, 128.7, 102.0, 100.6, 97.2, 84.6, 77.5, 77.1, 76.0, 75.4, 73.4, 73.0, 71.5, 70.7, 69.6, 68.2, 65.4, 63.6, 61.9, 53.4, 50.6, 43.4, 43.1, 42.0, 41.8, 38.3, 35.8, 29.8, 25.7, 25.4, 22.6, 22.5, 21.0, 20.6, 19.1, 18.1, 17.6.

Step 2b. Compound of Formula III: A=CH(OMe)2, R1=NMe2, R2=H, R3=Ac R4=C(O)CH2CHMe2, R5=H, $R^P$=H A solution of the compound from step 2a (97 mg, 0.099 mmol) in methanol (30 mL) was refluxed for 2 days. The solvent was evaporated under vacuum to give the crude title compound.

MS (ESI) m/z 877 (M+H)$^+$.

Example 3

Compound of Formula II: A=CH(OMe)2, R1=NH2, R2=H, R3=Ac, R4=C(O)CH2CHMe2, R5=H, $R^P$=H Step 3a. Compound of Formula XI of Scheme 2 (A=CH(OMe)2, R3=Ac, R4=C(O)CH2CHMe2, C10C11-anhydro, $R^P$=Ac).

Into a solution of a compound of Formula IX of Scheme 2 (A=CH(OMe)2, R3=Ac, R4=C(O)CH2CHMe2, C10C11-anhydro, $R^P$=Ac) (500 mg, 0.56 mmol) in methylene chloride (8 mL) at −78° C. were added triethylamine (277 μL, 2.0 mmol) and methanesulfonyl chloride (77 μL, 1.0 mmol). The mixture was stirred at −78° C. for 30 minutes. Into the reaction mixture powder tetrabutylammonium azide (795 mg, 2.8 mmol) was added. The mixture was then allowed to stand at −20° C. overnight, quenched by addition of water, extracted with chloroform (2×50 mL). The combined extracts were dried (Na$_2$SO$_4$), filtered and concentrated under reduced pressure. Purification on silica (EtOAc:Hexanes/1:1) afforded the desired compound (420 mg, 82%).

MS (ESI) m/z: 915 (M+H)$^+$; $^{13}$C-NMR (100 MHz, CDCl$_3$): δ 172.8, 170.4, 170.1, 168.6, 101.7, 100.4, 96.9, 77.2, 76.9, 76.0, 75.6, 72.5, 71.4, 71.0, 70.8, 69.2, 67.8, 65.6, 63.4, 61.7, 53.4, 49.8, 43.2, 41.5, 39.7, 39.2, 32.8, 31.0, 30.9, 29.8, 29.6, 25.4, 25.2, 22.4, 22.3, 21.6, 20.7, 20.2, 19.8, 17.9, 15.8.

Step 3b. Compound of Formula II: A=CH(OMe)2, R1=NH2, R2=H, R3=Ac, R4=C(O)CH2CHMe2, R5=H, $R^P$=Ac A solution of the compound from step 3a and triphenylphosphine (263 mg, 1.0 mmol) in THF (5 mL) was heated to reflux for 10 hours; water (0.5 mL) was then added. Heating was continued for 15 hours. The solvents were removed under reduced pressure to give the resulting crude amine.

(MS (ESI) m/z: 889 [M+H$^+$]).

Step 3c. Compound of Formula II: A=CH(OMe)2, R1=NH2, R2=H, R3=Ac, R4=C(O)CH2CHMe2, R5=H, $R^P$=H.

A solution of the crude amine from step 3b in methanol is refluxed for two days to give the title compound.

Example 4

Compound of Formula II: A=CH(OMe)2, R1=NMe2, R2=H, R3=Ac, R4=C(O)CH2CHMe2, R5=H, $R^P$=H Step 4a. Compound of Formula II: A=CH(OMe)2, R1=NMe2, R2=H, R3=Ac, R4=C(O)CH2CHMe2, R5=H, $R^P$=Ac.

The crude product of Step 3b was taken up in CH$_3$CN (9.0 mL). Into the mixture were added an aqueous solution of 37% formaldehyde (0.41 mL, 5.0 mmol), acetic acid (85 mg, 1.41 mmol), and NaCNBH$_3$ (112 mg, 1.77 mmol). The mixture was stirred at room temperature overnight, taken up in chloroform, washed with a solution of saturated NaHCO$_3$, dried (Na$_2$SO$_4$), filtered, and concentrated under reduced pressure. The crude residue was purified on silica (EtOAc) to give the title compound (220 mg, 51% overall yield).

MS (ESI) m/z: 918 (M+H)$^+$. $^{13}$C-NMR (100 MHz, CDCl$_3$): δ 172.8, 170.2, 169.4, 168.5, 130.7, 130.3, 101.3, 100.3, 96.9, 84.4, 77.2, 76.9, 75.7, 74.6, 72.6, 71.0, 70.8, 69.7, 69.3, 67,8, 63.4, 61.6, 60.2, 49.3, 44.1, 43.2, 41.6, 38.1, 38.0, 31.0, 30.9, 29.4, 28.8, 25.4, 25.2, 22.3, 22.3, 21.5, 20.8, 19.6, 18.8, 17.8, 15.5, 14.1.

Step 4b. Compound of Formula II: A=CH(OMe)2, R1=NMe2, R2=H, R3=Ac, R4=C(O)CH2CHMe2, R5=H, $R^P$=H.

A solution of the compound from step 4a (220 mg, 0.24 mmol) in MeOH (2 mL) was heated to reflux for two days and concentrated to afford the title compound.

MS (ESI) m/z 876 (M+H)$^+$.

Example 5

Compound of Formula II: A=CHO, R1=NMe2, R2=H, R3=Ac, R4=C(O)CH2CHMe2, R5=H, $R^P$=H The compound from Example 4 was taken up in CH$_3$CN (10 mL) and TFA (75 μL, 1 mmol) was added. The resulting solution was stirred for 4 days, quenched by addition of a saturated solution of NaHCO$_3$, concentrated under reduced pressure, taken up in water and extracted with chloroform (3×30 mL). The combined extracts were dried (NaSO$_4$), filtered and concentrated under reduced pressure. Purification of the crude residue on silica (CH$_2$Cl$_2$:MeOH:NH$_4$OH/93:6:1) afforded the title compound (15 mg, 8%).

MS (ESI) m/z 829 (M+H)$^+$; $^{13}$C-NMR (100 MHz, CDCl$_3$): δ 201.3, 172.9, 170.9, 169.6, 131.4, 129.8, 104.0, 97.0, 91.8, 83.8, 77.9, 77.2, 75.9, 73.0, 71.6, 71.5, 71.1, 70.4, 69.6, 69.3, 68.7, 63.5, 62.2, 44.1, 43.3, 41.9, 41.7, 40.9, 38.4, 29.4, 29.3, 26.7, 25.6, 25.5, 25.3, 22.4, 21.0, 19.7, 18.8, 17.8, 17.7, 15.5.

Example 6

Compound of Formula II: A=CHO, R1=NHMe, R2=H, R3=Ac, R4=C(O)CH2CHMe2, R5=H, $R^P$=H Step 6a. Compound of Formula II: A=CH(OMe)2, R1=NHC(O)CF3, R2=H, R3=Ac, R4=C(O)CH2CHMe2, R5=H, $R^P$=Ac To a solution of the compound from Example 3 in CH$_2$Cl$_2$ at −78° C. is added triethylamine (2 eq), followed by triflouroacetic anhydride (1.2 eq). The mixture is stirred at −78° C. for 30 minutes, then quenched by addition of water, and extracted with CH$_2$Cl$_2$. The organic layer is dried over Na$_2$SO$_4$. Removal of the solvent and column chromatography on silica gel column provides the title compound.

Step 6b. Compound of Formula II: A=CH(OMe)2, R1=NMeC(O)CF3, R2=H, R3=Ac, R4=C(O)CH2CHMe2, R5=H, $R^P$=Ac To a solution of the compound from Step 6a in DMF at 0° C. is added NaH (1.1 eq). The mixture is stirred at 0° C. for 15 min. Iodomethane (1.2 eq) is added. The mixture is stirred for another 15 minutes, then quenched by addition of a saturated solution of NH$_4$Cl, diluted with H$_2$O, and extracted with CH$_2$Cl$_2$. The organic layer is dried over Na$_2$SO$_4$. Removal of the solvent and column chromatography on silica gel column provides the title compound.

Step 6c. Compound of Formula II: A=CHO, R1=NMeC(O)CF3, R2=H, R3=Ac, R4=C(O)CH2CHMe2, R5=H, $R^P$=OAc The title compound is prepared from the compound of Step 6b according to the procedure described in step 1i.

Step 6d. Compound of Formula II: A=CHO, R1=NHMe, R2=H, R3=Ac, R4=C(O)CH2CHMe2, R5=H, $R^P$=H To a solution of the compound from Step 6c in MeOH (0.2M) is added a solution of 2M NH$_3$ in MeOH (2.0 eq). The mixture is stirred at room temperature overnight. Removal of the solvents under reduced pressure provides the title compound.

Example 7

Compound of Formula II: A=CHO, R1=NMeCH2C≡CH, R2=H, R3=Ac, R4=C(O)CH2CHMe2, R5=H, $R^P$=H To a solution of the compound from Example 9 in CH$_2$Cl$_2$ at room temperature is added N,N-diisopropylethylamine, followed by propargyl bromide. The mixture is stirred at room temperature overnight, taken up in ethyl acetate, washed with a solution of saturated aqueous Na$_2$HCO$_3$, with brine and dried over Na$_2$SO$_4$. Removal of the solvent and column chromatography on silica gel column provides the title compound.

Example 8

Compound of Formula II: A=CHO, R1=NMeCH2CH=CH2, R2=H, R3=Ac, R4=C(O)CH2CHMe2, R5=H, $R^P$=H The title compound is prepared according to the procedure of Example 7, replacing propargyl bromide with allyl bromide.

Example 9

Compound of Formula II: A=CHO, R1=NMeCH2(2-thienyl), R2=H, R3=Ac, R4=C(O)CH2CHMe2, R5=H, $R^P$=H The title compound is prepared according to the procedure of Example 7, replacing propargyl bromide with 2-thienylmethyl bromide.

Example 10

Compound of Formula II: A=CHO, R1=NMeCH2(2-furanyl), R2=H, R3=Ac, R4=C(O)CH2CHMe2, R5=H, $R^P$=H The title compound is prepared according to the procedure of Example 7, replacing propargyl bromide with furfuryl bromide.

Example 11

Compound of Formula II: A=CHO, R1=NMeCH2(4-chlorophenyl), R2=H, R3=Ac, R4=C(O)CH2CHMe2, R5=H, $R^P$=H To a solution of the compound from Example 6 in MeOH is added 4-chlorobenzaldehyde, excess NaCNBH$_4$ and enough acetic acid to give a pH 4 at room temperature. The reaction mixture is stirred at room temperature for 4–8 hours. The mixture is cooled to 0° C. and neutralized with a solution of saturated aqueous NaHCO$_3$ and is extracted with CH$_2$Cl$_2$. The organic layer is dried over Na$_2$SO$_4$. Removal of the solvents and column chromatography on silica gel provides the title compound.

Example 12

Compound of Formula II: A=CHO, R1=NMeCH2(2-pyridyl), R2=H, R3=Ac, R4=C(O)CH2CHMe2, R5=H, $R^P$=H The title compound is prepared according to the procedure of Example 11, replacing 4-chlorobenzaldehyde with 2-pyridinecarboxaldehyde.

Example 13

Compound of Formula II: A=CHO, R1=NMeCH2(3-quinolyl), R2=H R3=Ac, R4=C(O)CH2CHMe2, R5=H, $R^P$=H The title compound is prepared according to the procedure of Example 11, replacing 4-chlorobenzaldehyde with 3-quinolinecarboxaldehyde.

Example 14

Compound of Formula II: A=CHO, R1= NMeCH2CH=CH(phenyl), R2=H, R3=Ac, R4=C(O)CH2CHMe2, R5=H, $R^P$=H The title compound is prepared according to the procedure of Example 11, replacing 4-chlorobenzaldehyde with cinnamaldehydes.

Example 15

Compound of Formula II: A=CHO, R1= NMeCH2CH=CH(2-pyridyl), R2=H, R3=Ac, R4=C(O)CH2CHMe2, R5=H, $R^P$=H The title compound is prepared according to the procedure of Example 11, replacing 4-chlorobenzaldehyde with 3-(2-pyridyl)acrolein.

Example 16

Compound of Formula II: A=CHO, R1= NMeCH2C≡C(3-quinolyl), R2=H, R3=Ac, R4=C(O)CH2CHMe2, R5=H, $R^P$=H The title compound is prepared according to the procedure of Example 11, replacing 4-chlorobenzaldehyde with 3-(3-quinolyl)propynaldehyde.

Example 17

Compound of Formula II: A=CH2OH, R1=NMe2, R2=H, R3=Ac, R4=C(O)CH2CHMe2, R5=H, $R^P$=H A solution of the compound from Example 5 in methanol at 0° C. is treated with NaBH$_4$ and stirred at 0° C. for 1 hour. The reaction mixture is taken up in CH$_2$Cl$_2$ and is washed with water, brine and dried over Na$_2$SO$_4$. Removal of the solvents and column chromatography on a silica gel column provide the title compound.

Example 18

Compound of Formula II: A=CH2N(CH3)CH2Ph, R1=NMe2, R2=H, R3=Ac R4=C(O)CH2CHMe2, R5=H, $R^P$=H A solution of the compound from Example 5 in methanol is treated with N-methylbenzyl amine, excess NaCNBH$_3$ and enough acetic acid to give a pH 4 at room temperature. The reaction mixture is stirred at room temperature for 4–8 hours. The mixture is cooled to 0° C. and treated with saturated aqueous NaHCO$_3$ to give pH 7–8 and is extracted with CH$_2$Cl$_2$. The organic layer is washed with brine and dried over Na$_2$SO$_4$. Removal of the solvents and column chromatography on a silica gel column provide the title compound.

Example 19

Compound of Formula II: A=CH2N(CH3)CH2CH2Ph, R1=NMe2, R2=H, R3=Ac, R4=C(O)CH2CHMe2, R5=H, $R^P$=H The title compound is prepared according to the procedure of Example 18, replacing N-methylbenzylamine with N-methylphenethylamine.

Example 20

Compound of Formula II: A=CH2N(CH3)CH2CH2CH2Ph, R1=NMe2, R2=H, R3=Ac, R4=C(O)CH2CHMe2, R5=H, $R^P$=H The title compound is prepared according to the procedure of Example 18, replacing N-methylbenzylamine with N-methylphenpropylamine.

Example 21

Compound of Formula II: A=CH2N(CH3)CH2CH=CH2R1=NMe2, R2=H, R3=Ac, R4=C(O)CH2CHMe2, R5=H, $R^P$=H The title compound is prepared according to the procedure of Example 18, replacing N-methylbenzylamine with HN(CH3)CH2CH=CH2.

Example 22

Compound of Formula II: A=CH2N(CH3)CH2C≡CH, R1=NMe2, R2=H, R3=Ac, R4=C(O)CH2CHMe2, R5=H, $R^P$=H The title compound is prepared according to the procedure of Example 18, replacing N-methylbenzylamine with HN(CH3)CH2C≡CH,

Example 23

Compound of Formula II: A=CH2N(CH3)CH2CH=CH(3-quinolyl), R1=NMe2, R2=H, R3=Ac, R4=C(O)CH2CHMe2, R5=H, $R^P$=H The title compound is prepared according to the procedure of Example 18, replacing N-methylbenzylamine with HN(CH3)CH2CH=CH(3-quinolyl).

Example 24

Compound of Formula II: A=CH2N(CH3)CH2C≡C(5-pyrimidine), R1=NMe2, R2=H, R3=Ac, R4=C(O)CH2CHMe2, R5=H, $R^P$=H The title compound is prepared according to the procedure of Example 18, replacing N-methylbenzylamine with HN(CH3)CH2C≡C(5-pyrimidine).

Example 25

Compound of Formula II: A=CH2N(CH3)CH2C≡C(2-thienyl-(2-pyridyl)), R1=NMe2. 2=H, R3=Ac, R4=C(O)CH2CHMe2, R5=H, $R^P$=H The title compound is prepared according to the procedure of Example 18, replacing N-methylbenzylamine with HN(CH3)CH2C≡C(2-thienyl-(2-pyridyl)).

Example 26

Compound of Formula II: A=CH2N(CH3)CH2C≡C(3,5-dichlorophenyl), R1=NMe2, R2=H, R3=Ac, R4=C(O)CH2CHMe2, R5=H, $R^P$=H The title compound is prepared according to the procedure of Example 18, replacing N-methylbenzylamine with HN(CH3)CH2C≡C(3,5-dichlorophenyl).

Example 27

Compound of Formula II: A=CH2N(CH3)CH2C≡C(4-fluorophenyl), R1=NMe2, R2=H, R3=Ac, R4=C(O)CH2CHMe2, R5=H, $R^P$=H The title compound is prepared according to the procedure of Example 18, replacing N-methylbenzylamine with HN(CH3)CH2C≡C(4-fluorophenyl).

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by the Formula:

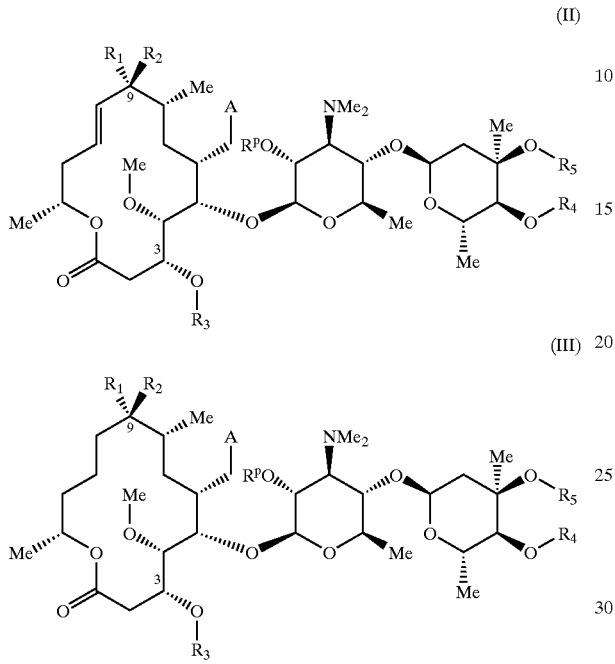

or a pharmaceutically acceptable salt, ester and prodrug thereof, wherein

A is selected from the group consisting of;
(1) —CHO, or a protected aldehyde
(2) —CH$_2$X, where X is selected from the group consisting of;
  a. hydroxy or protected hydroxy,
  b. halogen,
  c. —NR7R8, wherein R7 and R8 are each independently selected from hydrogen, aryl, substituted aryl, heterocyclic, substituted heterocyclic, C1–C6-alkyl, optionally substituted with aryl, substituted aryl, heterocyclic or substituted heterocyclic, C2–C6-alkenyl, optionally substituted with aryl, substituted aryl, heterocyclic or substituted heterocyclic and C2–C6-alkynyl, optionally substituted with aryl, substituted aryl, heterocyclic or substituted heterocyclic; or R7 and R8 taken together with the nitrogen atom to which they are connected form a 3- to 7-membered ring which, may optionally contain a hetero function selected from the group consisting of —O—, —NH—, —N(C1–C6-alkyl)—, —N(aryl), —N(heteroaryl), —S—, —S(O)— and —S(O)2—,
  d. —NR7C(O)—R9, where R7 is as previously defined and R9 is selected from the group consisting of;
    i. C1–C6-alkyl, optionally substituted with aryl, substituted aryl, heterocyclic or substituted heterocyclic,
    ii. aryl,
    iii. substituted aryl,
    iv. heterocyclic, and
    v. substituted heterocyclic,
  e. —S(O)$_n$—(C1–C6-alkyl), optionally substituted with aryl, substituted aryl, heterocyclic, or substituted heterocyclic, where n=0, 1 or 2,
  f. —S(O)$_n$—(C2–C6-alkenyl), optionally substituted with aryl, substituted aryl, heterocyclic or substituted heterocyclic, where n is as previously defined,
  g. —S(O)$_n$—(C2–C6-alkynyl), optionally substituted with aryl, substituted aryl, heterocyclic or substituted heterocyclic, where n is as previously defined
  h. —S(O)$_n$-(aryl or heterocyclic), where n is as previously defined, and
  i. —O -(aryl or heterocyclic),
(3) substituted or unsubstituted imidazole, arylimidazole or heteroarylimidazole,
(4) substituted or unsubstituted oxazole, aryloxazole or heteroaryloxazole,
(5) substituted or unsubstituted thioxazole, arylthioxazole or heteroarylthioxazole,
(6) substituted or unsubstituted imidazoline, arylimidazoline or heteroarylimidazoline,
(7) substituted or unsubstituted oxazoline, aryloxazoline or heteroaryloxazoline, and
(8) substituted or unsubstituted thioxazoline, arylthioxazoline or heteroarylthioxazoline, One of R1 and R2 is hydrogen and the other is —NR7R8, where R7 and R8 are as previously defined R3, R4 and R5 are each independently selected from the group consisting of;
(1) hydrogen,
(2) a hydroxy protecting group, and
(3) C(O)—C1–C12 alkyl, optionally substituted with aryl, substituted aryl, heterocyclic, substituted heterocyclic, —O—R7 or —NR7R8, where R7 and R8 are as previously defined; and R$^p$ is hydrogen or a hydroxy protecting group.

2. A compound according to claim 1 which is represented by Formula II.

3. A compound according to claim 2 wherein A=CHO, R1=NMe2, R2=H, R3=Ac, R4=C(O)CH2CHMe2, R5=H, R$^P$=H.

4. A compound according to claim 2 wherein A=CH(OMe)2, R1=NMe2, R2=H, R3=Ac, R4=C(O)CH2CHMe2, R5=H, R$^P$=H.

5. A compound according to claim 1 which is represented by Formula III.

6. A compound according to claim 5 wherein A=CHO, R1=NMe2, R2=H, R3=Ac, R4=C(O)CH2CHMe2, R5=H, R$^P$=H.

7. A compound according to claim 5 wherein A=CH(OMe)2, R1=NMe2, R2=H, R3=Ac, R4=C(O)CH2CHMe2, R5=H, R$^P$=H.

8. A compound according to claim 1 which is selected from the group consisting of:

Compound of Formula III: wherein A=CHO, R1=NMe2, R2=H, R3=Ac, R4=C(O)CH2CHMe2, R5=H, R$^P$=H Compound of Formula III: wherein A=CH(OMe)2, R1=NMe2, R2=H R3=Ac, R4=C(O)CH2CHMe2, R5=H, R$^P$=H Compound of Formula II: A=CH(OMe)2, R1=NH2, R2=H, R3=Ac, R4=C(O)CH2CHMe2, R5=H, R$^P$=H Compound of Formula II: wherein A=CH(OMe)2, R1=NMe2, R2=H, R3=Ac, R4=C(O)Ch2CHMe2, R5=H, R$^P$=H Compound of Formula II: wherein A=CHO, R1=NMe2, R2=H R3=Ac, R4=C(O)CH2CHMe2, R5=H, R$^P$=H Compound of Formula II: A=CHO, R1=NHMe, R2=H, R3=Ac, R4=C(O)CH2CHMe2, R5=H, R$^P$=H Compound of Formula II: A=CHO, R1=NMeCH2C≡CH, R2=H, R3=Ac, R4=C(O)CH2CHMe2, R5=H, R$^P$=H Compound of Formula II: A=CHO, R1=NMeCH2CH=CH2, R2=H, R3=Ac, R4=C(O)CH2CHMe2, R5=H, R$^P$=H Compound of Formula II: A=CHO, R1=NMeCH2(2-thienyl), R2=H, R3=Ac, R4=C(O)CH2CHMe2, R5=H, R$^P$=H Compound of Formula II: A=CHO, R1=NMeCH2(2-furanyl), R2=H, R3=Ac, R4=C(O)CH2CHMe2, R5=H, R$^P$=H Compound of Formula II: A=CHO, R1=NMeCH2(4-chlorophenyl), R2=H, R3=Ac, R4=C(O)CH2CHMe2, R5=H, R$^P$=H Compound of Formula II: A=CHO, R1=NMeCH2(2-pyridyl), R2=H, R3=Ac, R4=C(O)CH2CHMe2, R5=H, R$^P$=H Compound of Formula II: A=CHO, R1=NMeCH2(3-quinolyl), R2=H, R3=Ac, R4=C(O)CH2CHMe2, R5=H, R$^P$=H Compound of Formula II: A=CHO, R1=NMeCH2CH=CH(phenyl), R2=H, R3=Ac, R4=C(O)CH2CHMe2, R5=H, R$^P$=H Compound of Formula II: A=CHO, R1=NMeCH2CH=CH(2-pyridyl), R2=H, R3=Ac, R4=C(O)CH2CHMe2, R5=H, R$^P$=H Compound of Formula II: A=CHO, R1=NMeCH2C≡C(3-quinolyl), R2=H, R3=Ac, R4=C(O)CH2CHMe2, R5=H, R$^P$=H Compound of Formula II: A=CH2OH, R1=NMe2, R2=H, R3=Ac, R4=C(O)CH2CHMe2, R5=H, R$^P$=H Compound of Formula II: A=CH2N(CH3)CH2Ph, R1=NMe2, R2=H, R3=Ac, R4=C(O)CH2CHMe2, R5=H, R$^P$=H Compound of Formula II: A=CH2N(CH3)CH2CH2Ph, R1=NMe2, R2=H, R3=Ac, R4=C(O)CH2CHMe2, R5=H, R$^P$=H Compound of Formula II: A=CH2N(CH3)CH2CH2CH2Ph, R1=NMe2, R2=H, R3=Ac, R4=C(O)CH2CHMe2, R5=H, R$^P$=H Compound of Formula II: A=CH2N(CH3)CH2CH=CH2, R1=NMe2, R2=H, R3=Ac, R4=C(O)CH2CHMe2, R5=H, R$^P$=H Compound of Formula II: A=CH2N(CH3)CH2C≡CH, R1=NMe2, R2=H, R3=Ac, R4=C(O)CH2CHMe2, R5=H, R$^P$=H Compound of Formula II: A=CH2N(CH3)CH2CH=CH (3-quinolyl), R1=NMe2, R2=H, R3=Ac, R4=C(O) CH2CHMe2, R5=H, R$^P$=H Compound of Formula II: A=CH2N(CH3)CH2C≡C(5-pyrimidine), R1=NMe2, R2=H, R3=Ac, R4=C(O) CH2CHMe2, R5=H, R$^P$=H Compound of Formula II: A=CH2N(CH3)CH2C≡C(2-thienyl-(2-pyridyl)), R1=NMe2, R2=H, R3=Ac, R4=C (O)CH2CHMe2, R5=H, R$^P$=H Compound of Formula II: A=CH2N(CH3)CH2C≡C(3, 5-dichlorophenyl), R1=NMe2, R2=H, R3=Ac, R4=C (O)CH2CHMe2, R5=H, R$^P$=H Compound of Formula II: A=CH2N(CH3)CH2C≡C(4-fluorophenyl), R1=NMe2, R2=H, R3=Ac, R4=C(O) CH2CHMe2, R5=H, R$^P$=H.

9. A pharmaceutical composition for treating bacterial infections comprising a therapeutically effective amount of a compound of claim 1 or a pharmaceutically acceptable salt, ester or prodrug thereof in combination with a pharmaceutically acceptable carrier.

10. A method for treating bacterial infections comprising administering to a mammal in need of such treatment a pharmaceutical composition comprising a pharmaceutically effective amount of a compound of claim 1 or a pharmaceutically acceptable salt, ester or prodrug thereof.

11. A process for preparing a compound represented by the Formula

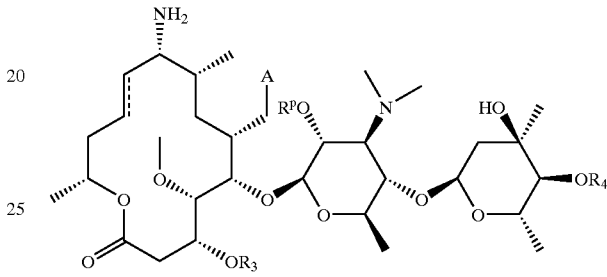

wherein A, R3, R4 and R$^P$ are as defined in claim 1 comprising the steps (a) reacting a compound represented by the Formula

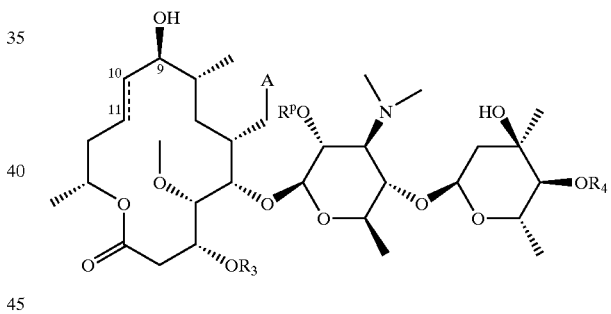

wherein A, R3, R4 and R$^P$ are as defined in claim 1 with mesyl chloride or tosyl chloride in an organic solvent to provide a compound represented by the Formula

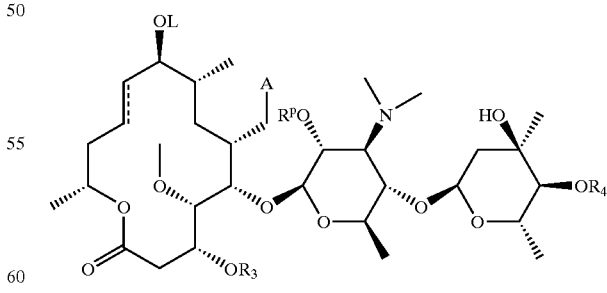

wherein A, R3, R4 and R$^P$ are as defined in claim 1 and L is mesyl or tosyl (b) reacting the product of step (a) with an azide nucleophile in an organic solvent to provide a compound represented by the Formula

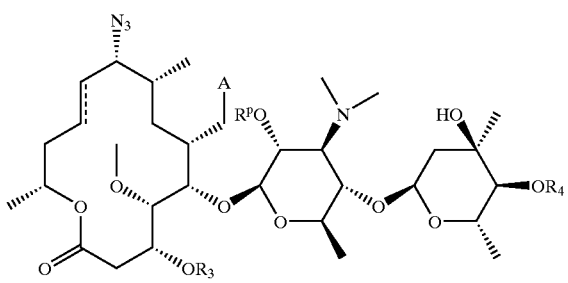

wherein A, R3, R4 and $R^p$ are as defined in claim 1, and (c) reducing the product of step (b) by reacting said product with a reducing agent in an organic solvent.

12. A process for preparing a compound represented by Formula II or III as defined in claim 1 comprising (a) reacting a compound represented by the Formula

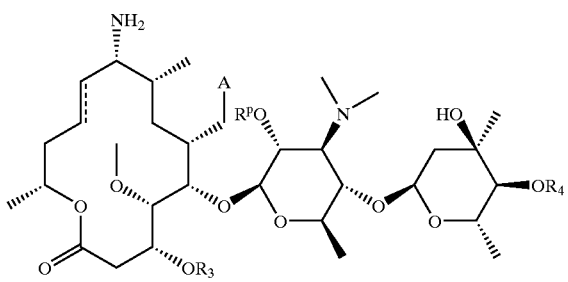

wherein A, R3, R4 and $R^p$ are as defined in claim 1 with an aldehyde according to a reductive amination method.

13. A process for preparing a compound represented by Formula II or III as defined in claim 1 comprising (a) reacting a compound represented by the Formula

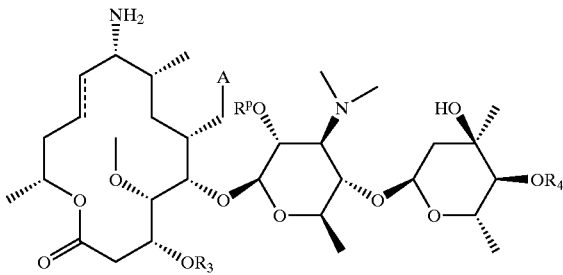

wherein A, R3, R4 and $R^p$ are as defined in claim 1 with an alkyl halide in an organic solvent at from room temperature to about 100° C.

14. A process for preparing a compound represented by Formula II or III as defined in claim 1 wherein A=—CH2NR7R8 and R1, R2, R3, R4, R5 and $R^p$ are as defined in claim 1 comprising (a) reacting a compound represented by Formula II or III as defined in claim 1 wherein A=CHO and R1, R2, R3, R4, R5 and $R^p$ are as defined in claim 1 with HNR7R8 in the presence of sodium cyanoborohydride according to a reductive amination method.

* * * * *